United States Patent [19]

Weitemeyer et al.

[11] Patent Number: 5,146,005
[45] Date of Patent: Sep. 8, 1992

[54] CATIONICALLY CURABLE OXALKYLENE ETHERS, METHOD FOR THEIR SYNTHESIS AND THEIR USE AS CASTING COMPOUNDS, COATING COMPOSITIONS OR AS REACTIVE DILUENTS FOR EPOXIDE RESINS

[75] Inventors: Christian Weitemeyer; Hardi Döhler, both of Essen, Fed. Rep. of Germany

[73] Assignee: TH. Goldschmidt AG, Essen, Fed. Rep. of Germany

[21] Appl. No.: 582,680

[22] Filed: Sep. 13, 1990

[30] Foreign Application Priority Data

Oct. 6, 1989 [DE] Fed. Rep. of Germany ... 8933420[U]

[51] Int. Cl.$^5$ .............................................. C07C 43/16
[52] U.S. Cl. ..................................... 568/616; 568/675
[58] Field of Search ................................. 568/675, 616

[56] References Cited

U.S. PATENT DOCUMENTS

| 4,173,511 | 11/1979 | Dietrich et al. | 176/36 |
| 4,518,788 | 5/1985 | Crivello | 560/64 |
| 4,617,238 | 10/1986 | Crivello et al. | 428/452 |
| 4,705,887 | 11/1987 | Crivello | 560/190 |

FOREIGN PATENT DOCUMENTS

| 0682727 | 3/1964 | Canada | 568/616 |
| 0061822 | 6/1982 | European Pat. Off. | |
| 2518652 | 11/1975 | Fed. Rep. of Germany | |
| 2518639 | 5/1979 | Fed. Rep. of Germany | |
| 2518656 | 6/1979 | Fed. Rep. of Germany | |

OTHER PUBLICATIONS

Geschwindigkeitsbestimmende Fakoren bei der kationischen UV-Härtung, pp. 803-807, Von J. V. Crivello Oct. 1987.

*Primary Examiner*—Marianne M. Cintins
*Assistant Examiner*—Michael Hydorn

*Attorney, Agent, or Firm*—Anderson, Kill, Oshinsky. P.C.

[57] ABSTRACT

New, cationically curable oxyalkylene ethers and the synthesis thereof are disclosed. The oxyalkylene ethers, are of the general, average formula

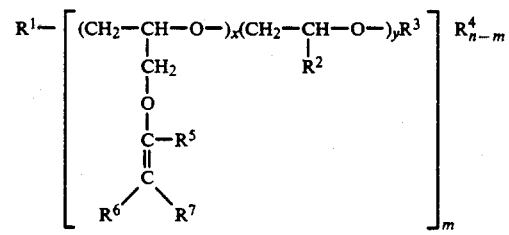

wherein
$R^1$ is an n-valent residual group derived from a compound $(R^1)H_n$ from which n active hydrogen atoms have been split off and is capable of entering into an addition reaction with oxiranes, or a univalent alkyl or aryl group, and $n \geq 1$;
$R^2$ is a hydrogen, hydrocarbon or $R^3OCH_2$— group;
$R^3$ and $R^4$ are each hydrogen, hydrocarbon or acyl groups, and $R^1$, $R^2$, $R^3$ and $R^4$ may have different meanings in the molecule;
$R^5$, $R^6$ and $R^7$ are each hydrogen or alkyl groups with 1 to 8 carbon atoms, or $R^5$ and $R^7$, or $R^6$ and $R^7$ together are a constituent of a cyclic, non-aromatic hydrocarbon group with 5 or 6 carbon atoms;
m is at least 1 and at most n;
x is the average molecule=3 to 100, and
y in the average molecule=0 to 100, provided that $3 \leq x+y < 150$.

They contain alkenyl groups and are useful as curable oligomers in casting compounds and coating agents and as reactive diluents for epoxide resins.

17 Claims, No Drawings

CATIONICALLY CURABLE OXALKYLENE ETHERS, METHOD FOR THEIR SYNTHESIS AND THEIR USE AS CASTING COMPOUNDS, COATING COMPOSITIONS OR AS REACTIVE DILUENTS FOR EPOXIDE RESINS

BACKGROUND OF INVENTION

This invention relates to cationically curable, optionally substituted, oxyalkylene ethers containing vinyl groups. The invention is directed, also, to methods for the synthesis of these oxyalkylene ethers and the use of these compounds as photochemically curable oligomers in casting compounds and coating agents and as reactive diluents for epoxide resins.

Aside from free radical polymerizing systems, in which curing is brought about by the action of UV, cationically curable systems containing epoxy or vinyl compounds have been developed in recent years. For these latter systems, curing is initiated particularly by diaryliodonium and triarylsulfonium salts. The advantages of cationically curing systems are that the curing reaction is insensitive to oxygen of the air, the film is cured rapidly and these systems do not contaminate the environment.

There is extensive patent literature dealing with this subject. The cationic curing of epoxy compounds with onium salts of 5th, 6th and 7th main groups of the periodic table is described, for instance, in the German Patents 25 18 656, 25 18 652 and 25 18 639. The cationic curing of vinyl monomers is the object of U.S. Pat. Nos. 4,617,238, 4,518,788 and 4,705,887.

Because they cure rapidly, can be processed economically and do not contaminate the environment, the UV-curable vinyl ether compounds have gained special attention. Such vinyl ether compounds can be synthesized in various ways. In a survey paper dealing with the "Rate-Determining Factors in Cationic UV Curing" in the journal Farbe und Lack, 1987, pages 803 to 807, the following possible reactions are given:

1. Base-catalyzed acetylene addition to diols according to Reppe

$$R-(O-CH=CH_2)_2$$

2. Phase transfer-catalyzed condensation of 2-chloroethyl vinyl ether with diols

HO—R—OH +

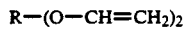

$$R-(O-CH_2-CH_2-O-CH=CH_2)_2$$

3. Catalyzed rearrangement of bis-allyl ethers into the corresponding bis-propenyl ethers

$$R-(O-CH=CH-CH_3)_2$$

The Reppe addition is not realizable from an economic point of view. For the second reaction, 2-chloroethyl ether is required, the use of which is undesirable for physiological reasons. It is common to all three types of reaction that invariably only one vinyl ether group per OH group of the alcohol can be introduced in to the molecule.

SUMMARY OF THE INVENTION

It is an object of the invention to provide compounds which have almost any number of optionally substituted vinyl ether groups, in order to be able to vary the curing and cross linking properties thereof, as desired.

Another object of the invention is to provide compounds having a predetermined, desired number of optionally substituted vinyl ether groups, which can be easily synthesized from available starting materials and which are physiologically as safe as possible.

A further object of the present invention is to provide a method for the synthesis of the new curable oxyalkylene ethers.

Still another object of the invention is to provide new curable oxyalkylene ethers useful as photocurable oligomers in casting compounds and coating agents and as reactive diluents for epoxide resins.

These and other objects of the invention are obtained by means of newly discovered, cationically curable oxyalkylene ethers which have the general, average formula

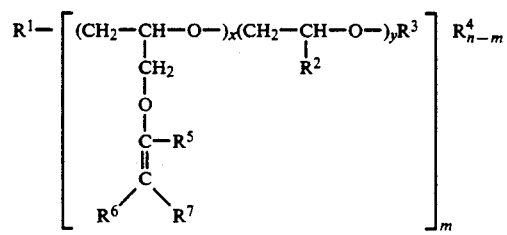

wherein

R$^1$ is an n-valent group derived from a compound (R$^1$)H$_n$ having n active hydrogen atoms and capable of entering into an addition reaction with oxiranes, or a univalent alkyl or aryl group, wherein n≧1;

R$^2$ is a hydrogen, hydrocarbon or R$^3$OCH$_2$— group;

R$^3$ and R$^4$ are each hydrogen, hydrocarbon or acyl groups, and R$^1$, R$^2$, R$^3$ and R$^4$ groups may each have the same or different meanings in the molecule;

R$^5$, R$^6$ and R$^7$ are each hydrogen or alkyl groups with 1 to 8 carbon atoms, or R$^5$ and R$^7$, or R$^6$ and R$^7$ together are a constituent of a cyclic, non-aromatic hydrocarbon group with 5 or 6 carbon atoms;

m is at least 1 and at most n;

x in the average molecule=1 to 100 and y in the average molecule=0 to 100, provided that $$1 \leq x+y < 150.$$

DESCRIPTION OF THE INVENTION

R$^1$ is either an n-valent group derived from a compound (R$^1$)H$_n$ which has n active hydrogens and is capable of entering into an addition reaction, or R$^1$ is a univalent alkyl or aryl group.

As a compound (R$^1$)H$_n$ which is capable of entering into an addition reaction with oxiranes, water, ammonia, a monohydric or multihydric alcohol, a monohydric or multihydric phenol, a monobasic or multibasic carboxylic acid or a monohydric or multihydric amine is preferred.

Examples of such compounds are set forth in Table 1.

TABLE 1

| Compound $(R^1)H_n$ | $R^1$ Group | n |
|---|---|---|
| $CH_3OH$ | $CH_3O-$ | 1 |
| $H_2O$ | $-O-$ | 2 |
| $HOCH_2CH_2OH$ | $-OCH_2CH_2O-$ | 2 |
| $CH_2OH$<br>$\|$<br>$CHOH$<br>$\|$<br>$CH_2OH$ | $CH_2O-$<br>$\|$<br>$CHO-$<br>$\|$<br>$CH_2O-$ | 3 |
| $HO-C_6H_4-OH$ | $-O-C_6H_4-O-$ | 2 |
| $HOOC-CH_2CH_2CH_2CH_2-COOH$ | $-OOC-CH_2-CH_2-CH_2-CH_2-COO-$ | 2 |
| $C_2H_5NH_2$ | $C_2H_5N\diagup\diagdown$ | 2 |

The $R^1$ group thus is the residual group, which is formed when n hydrogen groups are split off from the compound $(R^1)H_n$.

Further examples of compounds with one or more active hydrogen atoms can be taken from the literature, for example, from published European Application 0 061 822.

Particularly preferred $(R^1)H_n$ compounds are monohydric, saturated, aliphatic alcohols with 1 to 13 carbon atoms, such as methanol, ethanol, propanol, butanol, i-butanol, hexanol, decanol and tridecanol.

Moreover, $(R^1)H_n$ compounds of monohydric, unsaturated alcohols with 3 to 13 carbon atoms, such as allyl alcohol, oleyl alcohol, 5-hexen-1-ol, 3-methyl-3-buten-1-ol and 2-hydroxymethyl-5-norbornene are preferred.

Furthermore, dihydric to hexahydric aliphatic alcohols with 2 to 6 carbon atoms are preferred. These include ethylene glycol, glycerin, sorbitol, trimethylolpropane, pentaerythritol and dipentaerythritol.

In addition, preferred compounds of formula $(R^1)H_n$ include aliphatic, saturated and unsaturated monobasic and multibasic carboxylic acids, such as acetic acid, lauric acid, oleic acid, fumaric acid, maleic acid, tartaric acid, adipic acid, phthalic acid and terephthalic acid.

Finally, the aliphatic monoamines and diamines with 1 to 7 carbon atoms are encompassed among compounds $(R^1)H_n$. Examples of these amines are monoalkyl- or dialkyl-substituted ethylenediamine, 1,3-propylenediamine, 1,3- or 1,4-butylenediamine, allyamine, 2-methylallylamine, phenylenediamines and hexamethylenediamines.

The $R^1$ group may also be a monovalent alkyl or aryl group. In that case, $R^1$ preferably is a lower alkyl group, particularly the methyl, or phenyl group for arye.

$R^2$ is a hydrogen, hydrocarbon or $R^3OCH_2$ group. Preferably, $R^2$ is a hydrogen or lower alkyl group with 1 to 4 carbon atoms, particularly a methyl or ethyl group.

$R^3$ is a hydrogen, hydrocarbon or acyl group. Preferably it is a hydrogen or lower alkyl group with 1 to 4 carbon atoms. As an acyl group, the acetyl group is preferred.

$R^4$ is a hydrogen, hydrocarbon or acyl group. Preferably $R^4$ is a hydrogen group or an alkyl group with 1 to 4 carbon atoms. As an acyl group, the acetyl group is once again preferred.

In the polymeric molecule, the individual $R^1$, $R^2$, $R^3$ and $R^4$ groups can each have a different meaning.

$R^5$, $R^6$ and $R^7$ are hydrogen or alkyl groups with 1 to 8 carbon atoms. Preferably the groups are hydrogen groups or lower alkyl groups especially with 1 to 4 carbon atoms. However, $R^5$ and $R^7$ or $R^6$ and $R^7$ can also be the common constituent of a cyclic, non-aromatic hydrocarbon group with 5 or 6 carbon atoms. In this case, preferably the $R^5$ and $R^7$ groups are constituents of such a cyclic ring, $R^6$ being a hydrogen group.

If the $R^6$ and $R^7$ groups are different, the possibility exists of forming cis and trans isomers. Both isomeric forms are usable within the intent of the invention.

m has a numerical value of at least 1 and, at most, is equal to n. If n is 1, the $R^4$ group is omitted.

x indicates the number of oxyalkylene units with laterally linked, optionally substituted vinyl groups. In the average molecule, x has a value of 1 to 100. Preferably, the product of m times x (m·x) is greater than 1.

y indicates the number of oxyalkylene units, which are free of vinyl groups. In the average molecule, y has a value of 0 to 100, with the proviso that $1 \leq x+y < 150$. The product of m times y (m·y) preferably is 0 to 25.

Examples of the inventive, cationically curable oxyalkylene ethers are given by the following formulas:

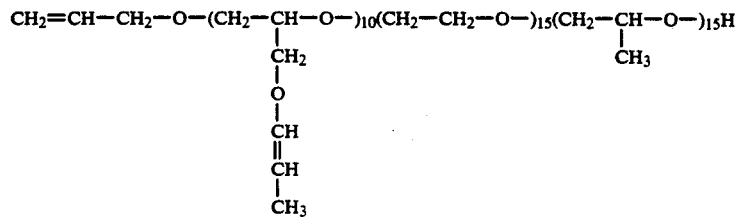

-continued

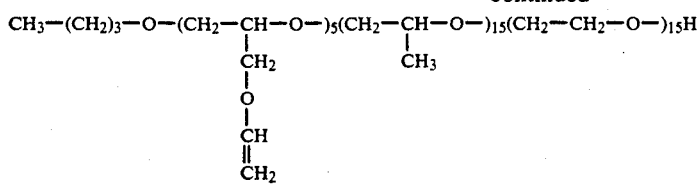

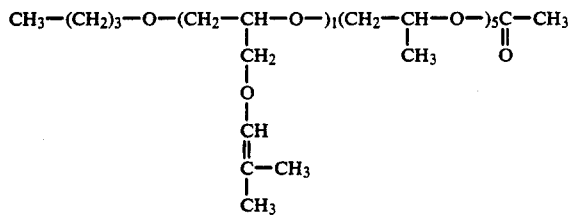

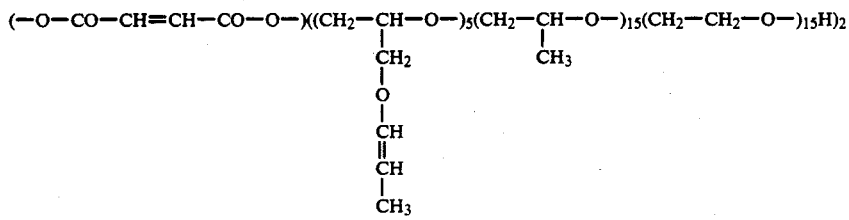

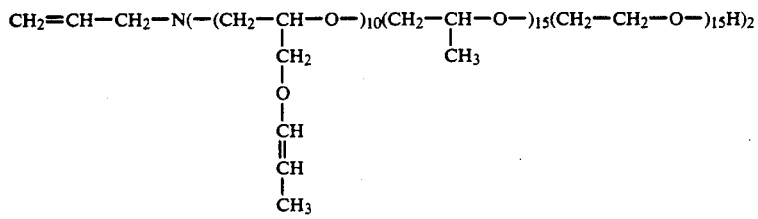

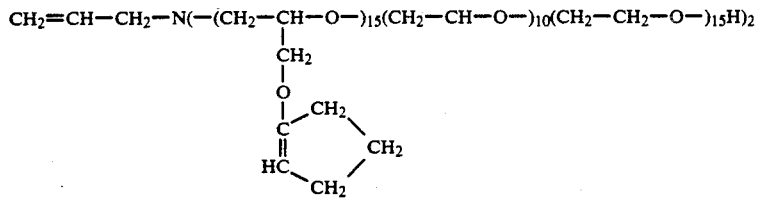

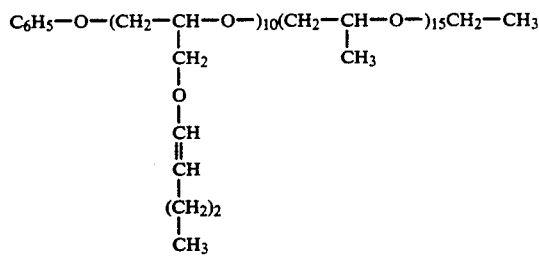

With reference to the synthesis of the new curable oxyalkylene ethers, which is one of the objects of the invention, a particularly preferred method of the synthesis is carried out as follows:

m·x moles of monomer of the general formula

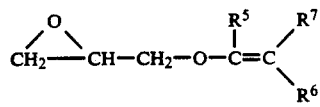

and, if necessary, y·m moles of monomer of the general formula

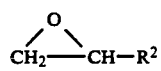

are subjected to a random or blockwise addition reaction under alkaline or essentially neutral conditions with 1 mole of a compound of the general formula $(R^1)H_n$ and the compounds obtained are optionally etherified totally or partially with an alkyl halide of the formula $R^3X$ or with a carboxylic acid anhydride of the formula $(R^3CO)_2O$ or with an acyl halide of the formula $R^3COX$, X being a halogen atom.

The addition reaction between alkylene oxides and compounds with active hydrogen is carried out in the usual manner, preferably under a pressure of 0.1 to 10 bar and optionally under an inert gas in a closed system. As catalyst, preferably alkali or alkaline earth alcoholates, particularly the corresponding salts of methanol or ethanol, as well as alkali hydroxides, such as KOH or NaOH, are used.

The addition reaction usually is carried out at a temperature of 50° to 200° C. and particularly at a temperature of 80° to 150° C.

The addition reaction can also be carried out using alkyl lithium compounds. The reaction then proceeds as follows:

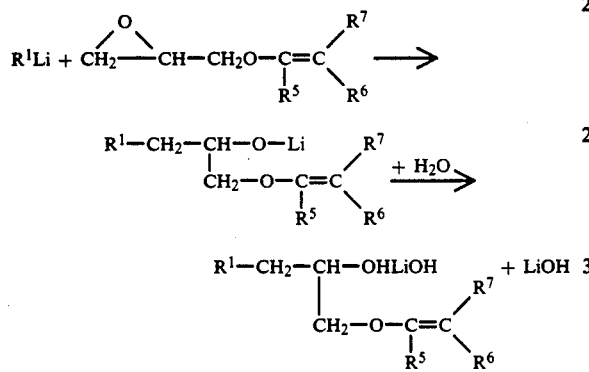

With this reaction, compounds are always formed, in which n has a value of 1 and the $R^4$ group thus is omitted.

Examples of suitable alkylene oxides with and without vinyl groups are

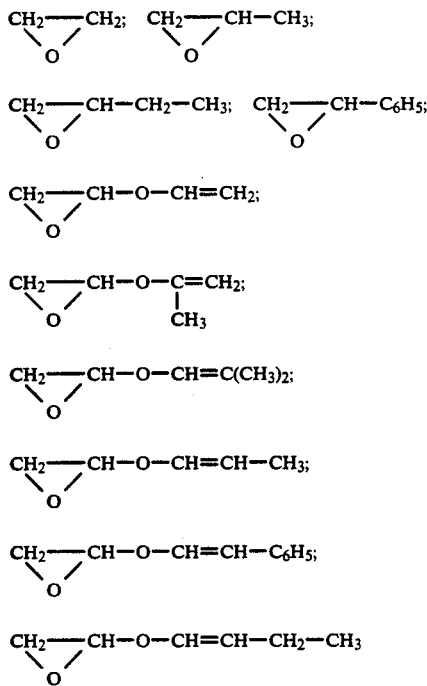

A further method of synthesis is characterized by the fact that compounds of the general, average formula

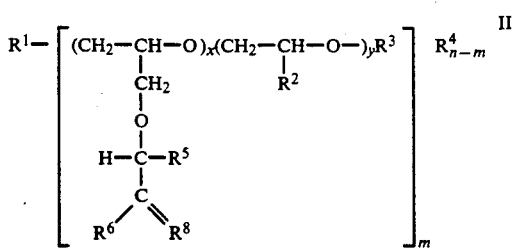

in which $R^1$, $R^2$, $R^3$, $R^4$, $R^5$ and $R^6$ have the meanings already given and x, y, n and m have the values already given while $R^8$ is an alkylene group, are rearranged in the usual manner.

The groups, subscripts and superscripts have the meanings already given. $R^8$ is a hydrocarbon group with 1 to 8 carbon atoms and two free bonds at a carbon atom, such as the $=CH_2$, $=CH-CH_3$ or $=CH-CH_2-CH_3$ group.

The rearrangement of the double bond in the alpha position to the carbon atom linked to the ether oxygen (rearrangement to the optionally substituted propenyl compound) is carried out by methods that are known. Preferably, the rearrangement is carried out by the action of alkali alcoholates or catalysts containing metal complexes or transition metals at temperatures of about 25° to 170° C., optionally in polar solvents.

The inventive methods have the advantages of proceeding in a simple manner using readily accessible starting materials and the use of the toxic chloroethyl compounds is avoided.

As to the use of the new compounds, which is also an object of the invention, after the addition of known photoinitiators, the inventive compounds are cured by the action of UV radiation. Examples of suitable initiators are the onium salts, particularly of compounds of the 5th to the 7th main group of the periodic table, such as aryl-substituted phosphonium, sulfonium and iodonium salts of strong acids or of non-salt-like compounds such as the ketosulfones.

Examples of photoinitiators of the onium salt type are:

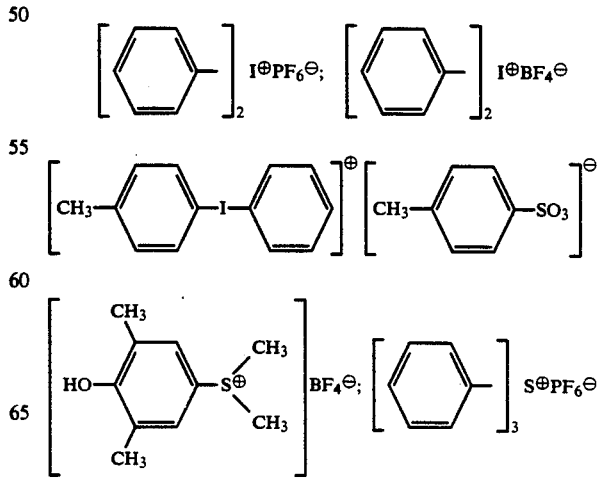

-continued

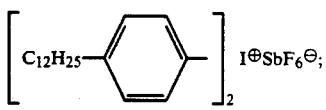

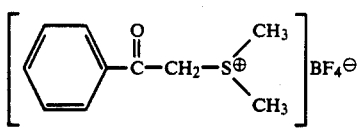

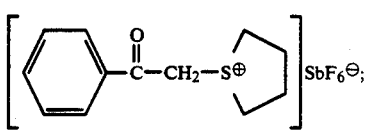

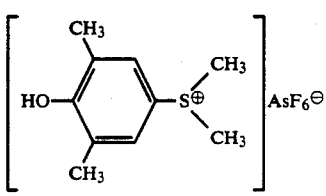

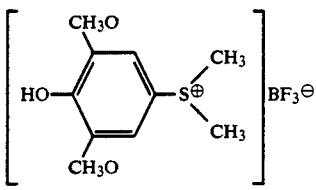

Particularly preferred intitiators are:

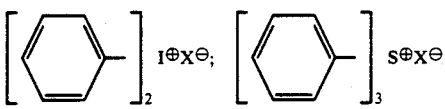

$X^\ominus = PF_6^\ominus; \ BF_4^\ominus; \ SbF_6^\ominus$

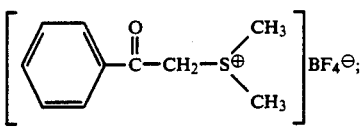

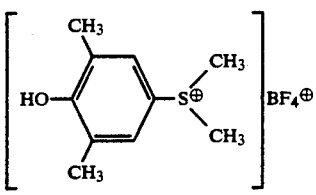

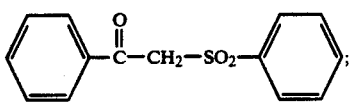

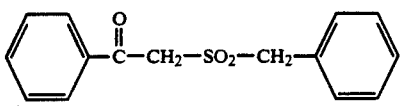

-continued

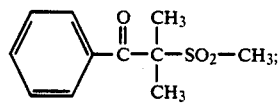

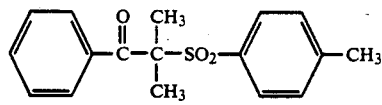

Moreover, heat curing using onium salts with organic oxidizing agents or soluble copper salts or chelates, such as is described in the U.S. Pat. No. 4,173,511, is possible. A different way of bringing about curing involves the use of compounds which release acids or Lewis acids at elevated temperatures, such as sulfonic acid salts, particularly amine salts, sulfonic acid esters and amine complexes of Lewis acids, such as the boron trifluoride triethylamine complex.

The initiators are added in an amount of about 0.5 to 10% by weight to a compond of the invention.

The componds of the invention cure in a very short time (fractions of a second to several seconds) to tack-free, flexible or hard products. They can therefore be used in an advantageous manner as casting compounds, for example, for electronic components, as coating materials for planar carries and as reactive diluents for expoxy resins.

Compared to the known vinyl compounds of the state of the art, the compounds of the invention have the advantage that practically any number of optionally substituted vinyl groups can be arranged along the chain of the polymeric molecule. By these means, the curing rate and the cross-linking density can be adapted to the requirements arising from the particular use. A further advantage is that, when $R^3$ and $R^4$ represent a hydrogen atom, the compounds of the invention can undergo further reactions, for example with isocyanates.

For their application the compounds can be mixed with conventional additives, such as modifiers, pigments, fillers, flame retardants, etc.

The following examples further ilustrate the best mode currently contemplated for carrying out the invention; preferred synthesis methods are explained further and the properties of the inventive compounds are shown by application-related experiments. However, the illustrative examples must not be construed as limiting the invention in any manner.

EXAMPLE 1

To a stirred vessel, 66.6 g (0.9 moles) of butanol and 7 g (0.1 moles) of potassium methylate are added and overlaid with a blanket of nitrogen. At 100° C., 114 g (1 mole) of propenyl glycidyl ether are added dropwise at such a rate, that the temperature does not exceed 120° C. The reaction mixture is stirred for a further 3 hours at 100° C. and then neutralized with 13 g of 50% phosphoric acid. After filtration, the product is distilled under a reduced pressure until the temperature reaches 100° C., 175 g (95% of the theoretical yield) of a slightly yellowish, low viscosity product being obtained, which according to $^1$H-NMR has the following average formula

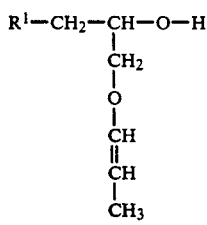

in which R¹ consists of 90% CH₃(CH₂)₃O— groups and 10% CH₃O— groups.

EXAMPLE 2

To a stirred vessel, 66.6 g (0.9 moles) of butanol and 7 g (0.1 moles) of potassium methylate are added and overlaid with a blanket of nitrogen. At 100° C., 342 g (3 moles) of propenyl glycidyl ether are added dropwise at such a rate, that the termperature does not exceed 120° C. The reaction mixture is stirred for a further 3 hours at 100° C. and treated with 50 g of finely powdered KOH. Methyl chloride is then passed in until it is no longer absorbed by the reaction mixture, which is then neutralized with 50% phosphoric acid. After filtration, the product is distilled under a reduced pressure up to a temperature of 100° C., 408 g (96% of the theoretical yield) of a slightly yellowish product of low viscosity being obtained, which according to ¹H-NMR has the following average formula

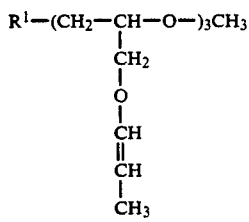

in which R¹ consists of 90% CH₃(CH₂)₃O groups and 10% CH₃O groups.

EXAMPLE 3

To a pressure vessel, 66.6 g (0.9 moles) of butanol and 7 g (0.1 moles) of potassium methylate are added and overlaid with a blanket of nitrogen at a pressure of 2 bar. At 100° C., 580 g (10 moles) of propylene oxide and 342 g (3 moles) of propenyl glycidyl ethers are passed in or added dropwise simultaneously at such a rate, that the pressure does not exceed 5 bar and the temperature does not exceed 120° C. The reaction mixture is stirred for a further 3 hours at 100° C. and then neutralized with 13 g of 50% phosphoric acid. After filtration, the product is distilled under reduced pressure up to a temperature of 100° C., 932 g (94% of the theoretical yield) of a slightly yellowish product of low viscosity being obtained, which according to ¹H-NMR has the average formula

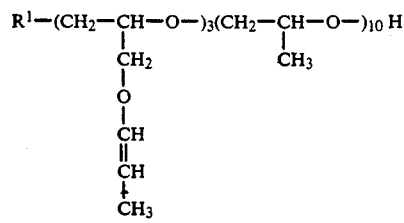

in which R¹ consists of 90% CH₃(CH₂)₃O— groups and 10% CH₃O— groups.

EXAMPLE 4

To a stirred vessel, 654 g (1 mole) of a butanol-started polyether having 10 units of propylene oxide and 7.0 g (0.1 mole) of potassium methylate are added and overlaid with a blanket of nitrogen. The methanol is then distilled off at 100° C. After that, 342 g (3 moles) of propenyl glycidyl ether are added dropwise at such a rate, that the temperature of 120° C. is not exceeded. The reaction mixture is stirred for a further 3 hours at 100° C. and then neutralized with 13 g of 50% phosphoric acid. After filtration, the product is distilled under reduced pressure until the temperature reaches 100° C., 926 g (93% of the theoretical yield) of a slightly yellowish, low viscosity product being obtained, which according to ¹H-NMR has the average formula

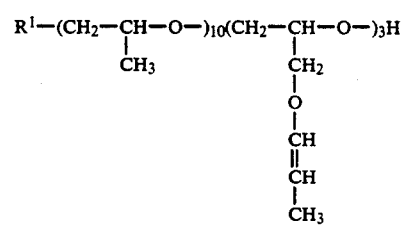

wherein R¹ is a CH₃(CH₂)₃O— group.

EXAMPLE 5

To a pressure vessel, 66.6 g (0.9 moles) of butanol and 7 g (0.1 moles) of potassium methylate are added and overlaid with a blanket of nitrogen at a pressure of 2 bar. At 100° C., 870 g (15 mole) of propylene oxide, 660 g (15 moles) of ethylene oxide and 1140 g (10 moles) of propenyl glycidyl ether are passed in or added dropwise simultaneously at such a rate, the pressure does not exceed 5 bar and the temperature does not exceed 120° C. The reaction mixture is stirred for a further 3 hours at 100° C. and then neutralized with 13 g of 50% phosphoric acid. After filtration, the product is distilled under a reduced pressure until the temperature reaches 100° C., 2,575 g (94% of the theoretical yield) of a slightly yellowish, viscous product being obtained, which according to ¹H-NMR has the average formula

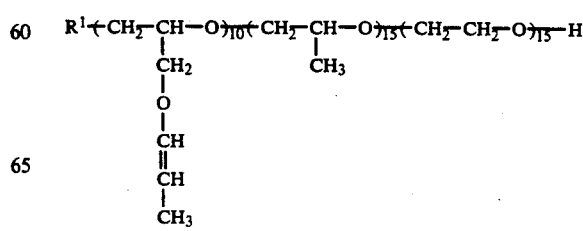

wherein $R^1$ consists of 90% $CH_3(CH_2)_3O-$ groups and 10% $CH_3O-$ groups.

EXAMPLE 6

To a pressure vessel, 120.6 g (0.9 moles) of trimethylolpropane and 7 g (0.1 moles) of potassium methylate are added and overlaid with a blanket of nitrogen. The methanol is then distilled off at 100° C. After that, the pressure is adjusted to 2 bar with nitrogen and 1,566 g (27 moles) of propylene oxide and 615.6 g (5.4 moles) of propenyl glycidyl ether are passed in or added dropwise simultaneously at 100° C. at such a rate, that the pressure does not exceed 5 bar and the temperature does not exceed 120° C. The reaction mixture is stirred for a further 3 hours at 100° C. and then neutralized with 13 g of 50% phosphoric acid. After filtration, the product is distilled under reduced pressure until the temperature reaches 100° C., 2,260 g (98% of the theoretical yield) of a yellowish product of moderate viscosity being obtained, which according to $^1$H-NMR has the following average formula

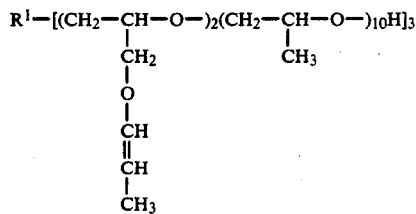

in which $R^1$ is the $CH_3-CH_2-C(CH_2O-)_3$ group.

EXAMPLE 7

To a stirred vessel, 66.6 g (0.9 moles) of butanol and 7 g (0.1 moles) of potassium methylate are added and overlaid with a blanket of nitrogen. At 100° C., 384 g (3 moles) of 1-methylpropenyl glycidyl ether are added dropwise at such a rate, that the temperature does not exceed 120° C. The reaction mixture is stirred for a further 3 hours at 100° C. and then neutralized with 13 g of 50% phosphoric acid. After filtration, the product is distilled under reduced pressure until the temperature reaches 100° C., 408 g (90% of the theoretical yield) of a slightly yellowish, low viscosity product being obtained, which according to $^1$H-NMR has the average formula

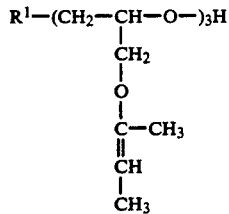

wherein $R^1$ consists of 90% of the $CH_3(CH_2)_3O-$ group and 10% of the $CH_3O-$ group.

EXAMPLE 8

To a pressure vessel, 66.6 g (0.9 moles) of butanol and 7 g (0.1 moles) of potassium methylate are added and overlaid with a blanket of nitrogen at a pressure of 2 bar. At 100° C., 580 g (10 moles) of propylene oxide and 300 g (3 moles) of vinyl glycidyl ether are passed in or added dropwise simultaneously at such a rate, that the pressure does not exceed 5 bar and the temperature does not exceed 120° C. The reaction is stirred for a further 3 hours at 100° C. and then neutralized with 13 g of 50% phosphoric acid. After filtration the product is distilled under reduced pressure up to a temperature of 100° C., 893 g of product (94% of the theoretical yield) of a slightly yellowish, low viscosity product being obtained, which according to $^1$H-NMR has the average formula

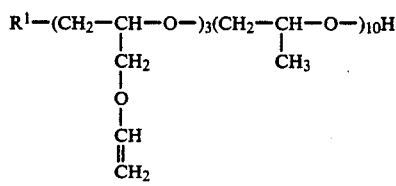

wherein $R^1$ consists of 90% $CH_3(CH_2)_3O-$ groups and 10% $CH_3O-$ groups.

EXAMPLE 9

To a stirred vessel, 66.6 g (0.9 moles) of butanol and 7 g (0.1 moles) of potassium methylate are added and overlaid with a blanket of nitrogen. At 100° C., 342 g (3 moles) of allyl glycidyl ether are added dropwise at such a rate, that the temperature does not exceed 120° C. The reaction mixture is stirred for a further 3 hours at 100° C. and then neutralized with 13 g of 50% phosphoric acid. After filtration, the product is distilled under reduced pressure up to a temperature of 100° C. and then stirred for 20 hours at 120° C. with 0.5 g of tris(triphenylphosphine)ruthenium(II) dichloride, 395 g (96% of the theoretical yield) of a slightly yellowish, low viscosity product being obtained, which according to $^1$H-NMR has the average formula

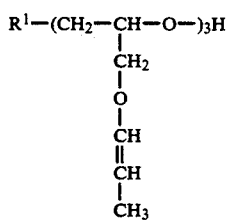

wherein $R^1$ consists of 90% $CH_3(CH_2)_3O-$ groups and 10% $CH_3O-$ groups.

EXAMPLE 10

Ethylenediamine (60 g, 1 mole) is added to a stirred vessel, which is then flushed with nitrogen. At 130° C., 501.6 g (4.4 moles) of propenyl glycidyl ether are then added dropwise at such a rate, that the temperature does not exceed 150° C. The reaction mixture is stirred for a further 3 hours at 130° C. and then distilled under a reduced pressure until the temperature reaches 130° C., 490 g (95% of the theoretical yield) of a slightly yellowish, low viscosity product being obtained, which according to $^1$H-NMR has the following average formula

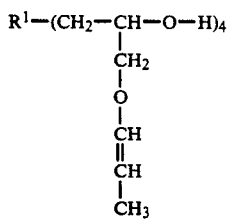

in which R¹ is the ethylenediamine group.

APPLICATION TESTS

The compounds of Examples 1 to 10 are well mixed with 2% by weight of diphenyl iodonium hexafluorophosphate and cured with a UV lamp supplied by Fusion Systems Corporation, Rockville, Md., U.S.A., Model I 300 B, at a distance of 53 mm on a glass plate in a layer 20 or 400 microns thick. The curing times, which are required to obtain a smudge-free surface, together with the film properties, are given in the following Table 2.

TABLE 2

| Compound | Curing Time(s) 20 μm | Curing Time(s) 400 μm | Film Properties 400 μm | Pencil Hardness (ECCA Standard) |
|---|---|---|---|---|
| 1 | 2 | 3 | solid | HB |
| 2 | 1 | 3 | hard, brittle | 2H |
| 3 | 2 | 5 | solid, flexible | 2B |
| 4 | 1 | 4 | solid, flexible | HB |
| 5 | 1 | 4 | soft, flexible | 2B |
| 6 | 2 | 5 | solid, hard | 3H |
| 7 | 1 | 3 | solid, hard | H |
| 8 | 1 | 3 | solid, hard | HB |
| 9 | 1 | 3 | solid, hard | H |
| 10* | 2 | 6 | soft, brittle | 2B |

*with 10 photoinitiator

The compounds of Examples 1, 2, 3, 6 and 9 are each mixed with 50% of bisphenol A diglycidyl ether (compound A) and cured with 4% diphenyl iodonium hexafluorophosphate as described in a 400 micron layer on a glass plate. The curing times and film properties are given in the following Table 3.

TABLE 3

| Mixture with Compound A | Curing Time (seconds) | Film Properties | Pencil Hardness (ECCA Standard) |
|---|---|---|---|
| Compound 1 | 12 | flexible | HB |
| Compound 2 | 5 | solid | B |
| Compound 3 | 8 | soft, flexible | HB |
| Compound 6 | 5 | flexible | B |
| Compound 9 | 4 | flexible | 2B |
| Compound A alone | 30 | soft, flexible | 3B |

In a further experiment, the diphenyl iodonium hexafluorophosphate, which was used as photoinitiator, was exchanged for a photoinitiator commercially obtainable under the name of NACURE X49-110, which is a blocked dinonylnaphthalenedisulfonic acid. It is used in an amount of 5% by weight and mixed with the compounds to be cured. The mixtures are cured as 400 micron layers on a glass plate at 120° C. In the following Table 4, the times that are required for the smudge-free curing of the mixtures, are given, as are the film properties and the hardness of the films.

TABLE 4

| Mixture with Compound A | Curing Time (min.) | Film Properties | Pencil Hardness (ECCA Standard) |
|---|---|---|---|
| Compound 1 | 22 | solid | HB |
| Compound 2 | 15 | hard | H |
| Compound 3 | 16 | soft, flexible | HB |
| Compound 6 | 15 | hard | 2H |
| Compound 9 | 12 | hard | H |
| Compound A alone | 3 | hard | H |

We claim:

1. A cationically curable oxyalkylene ether having the average formula

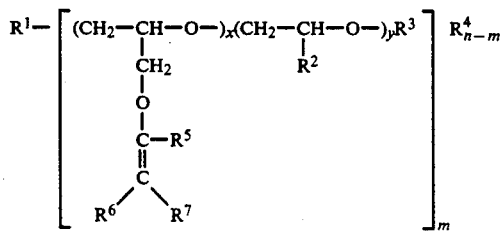

wherein
R¹ is an n-valent residual group derived from a compound $(R^1)H_n$ from which n active hydrogen atoms have been split off and is capable of entering into an addition reaction with oxiranes, or a univalent alkyl or aryl group, and $n \geq 1$;
R² is a hydrogen, hydrocarbon or $R^3OCH_2-$ group;
R³ and R⁴ are each hydrogen, hydrocarbon or acyl groups, and R¹, R², R³ and R⁴ are the same or different in the ether;
R⁵, R⁶ and R⁷ are each hydrogen or alkyl groups with 1 to 8 carbon atoms, or R⁵ and R⁷, or R⁶ and R⁷ together are a constituent of a cyclic, non-aromatic hydrocarbon group with 5 or 6 carbon atoms;
m is at least 1 and at most n;
x in the average molecule = 3 to 100, and
y in the average molecule = 0 to 100, provided that $3 \leq x+y < 150$.

2. The oxyalkylene ether according to claim 1, in which at least one of the R⁵, R⁶ and R⁷ groups is an alkyl group.

3. The oxyalkylene ether according to claim 1, in which at least one of the R⁶ group and the R⁷ group is an alkyl group.

4. The oxyalkylene ether according to claim 1, in which R⁵ and R⁶ are hydrogen groups and R⁷ is methyl group.

5. The oxyalkylene ether according to claim 1, in which R⁵ and R⁷ together are a constituent of a cyclic, non-aromatic hydrocarbon group with 5 or 6 carbon atoms and R⁶ is a hydrogen atom.

6. The oxyalkylene ether according to claim 1, in which $3 < x+y < 150$.

7. The oxyalkylene ether according to claim 1, in which x has an average value of 3 to 25.

8. The oxyalkylene ether according to claim 1, in which the compound $(R^1)H_n$ is selected from the group consisting of water, ammonia, a monohydric or multihydric alcohol, a monohydric or multihydric phenol, a monobasic or multibasic carboxylic acid and a monohydric or multihydric amine.

9. The oxyalkylene ether according to claim 1, in which the compound $(R^1)H_n$ is a monohydric, saturated aliphatic alcohol with 1 to 13 carbon atoms.

10. The oxyalkylene ether according to claim 1, in which the compound $(R^1)H_n$ is a monohydric, unsaturated alcohol with 3 to 13 carbon atoms.

11. The oxyalkylene ether according to claim 1, in which the average value of the product of m times x is greater than 3.

12. The oxyalkylene ether according to claim 1, in which the average value of the product of m times x is 3 to 25 and the average value of the product of m times y is 0 to 25.

13. The oxyalkylene ether according to claim 1, in which $R^2$ is a selected from the group consisting of hydrogen, a methyl, ethyl and $R^3OCH_2$— group and $R^3$ is hydrogen or an alkyl group.

14. A casting composition comprising a curable oligomer which is an oxyalkylene ether defined in claim 1.

15. A coating agent comprising an oxyalkylene ether defined in claim 1.

16. A reactive diluent useful for epoxide resins comprising an oxyalkylene ether defined in claim 1.

17. The oxyalkylene ether

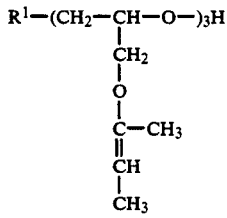

wherein $R^1$ comprises 90% of $CH_3(CH_2)_3O$—, and 10% of $CH_3O$—.

* * * * *